United States Patent [19]
Iwamoto et al.

[11] Patent Number: 6,138,514
[45] Date of Patent: Oct. 31, 2000

[54] TUBE FLAW DETECTING METHOD USING TWO PROBES

[75] Inventors: Keiichi Iwamoto; Kiyotaka Aoki; Hironori Ishii, all of Nagasaki; Shinichi Tsuji, Kitakyushu; Kinjiro Kobayashi, Nagasaki, all of Japan

[73] Assignees: Mitsubishi Heavy Industries, Ltd., Tokyo; Shin-Nippon Nondestructive Inspection Co., Kitakyushu; Kyusyugiken Co., Ltd., Nagasaki, all of Japan

[21] Appl. No.: 09/097,734

[22] Filed: Jun. 16, 1998

[30] Foreign Application Priority Data

Sep. 30, 1997 [JP] Japan ................................. 9-266351

[51] Int. Cl.⁷ .................................................. G01N 29/04
[52] U.S. Cl. .................................. 73/622; 73/598; 73/600
[58] Field of Search ............................... 73/596, 597, 598, 73/599, 600, 614, 615, 616, 618, 620, 622, 624, 628, 629, 632, 637, 638; 702/33, 35, 39

[56] References Cited

U.S. PATENT DOCUMENTS

| | | | |
|---|---|---|---|
| 3,302,453 | 2/1967 | Wood et al. ................................. | 73/624 |
| 3,885,419 | 5/1975 | Witte et al. ................................ | 73/600 |
| 4,669,310 | 6/1987 | Lester ........................................ | 73/597 |
| 4,679,437 | 7/1987 | Koike et al. ............................... | 73/622 |
| 4,685,334 | 8/1987 | Latimer ..................................... | 73/599 |
| 4,890,496 | 1/1990 | Birring et al. ............................. | 73/599 |
| 5,092,176 | 3/1992 | Buttram et al. ........................... | 73/599 |
| 5,681,996 | 10/1997 | White ........................................ | 73/622 |

*Primary Examiner*—Helen C. Kwok
*Attorney, Agent, or Firm*—Wenderoth, Lind & Ponack, L.L.P.

[57] ABSTRACT

A tube flaw detecting method detects a flaw portion in a heat exchanger tube constituting a boiler furnace wall using two probes, enabling one to carry out appropriate inspection work with a high efficiency. A transmitter probe and a receiver probe are juxtaposed in a circumferential direction, and an ultrasonic wave is transmitted from the transmitter probe to propagate. Repeated reflections occur at a tube inner surface and tube outer surface, and the wave is reflected at a crack extending in the circumferential direction to return, propagating likewise to be received by the receiver probe so that existence of the crack is confirmed. Thus, inspection work for a crack can be done with certainty with a simple arrangement.

20 Claims, 7 Drawing Sheets

F:WAVE SHAPE OF CRACK

NO CRACK

F: WAVE SHAPE OF CRACK

NO CRACK

TUBE FLAW DETECTING METHOD USING TWO PROBES

BACKGROUND OF THE INVENTION

1. Field of the Invention

The present invention relates to a tube flaw detecting method by which a flawed portion in a heat exchanger tube constituting a boiler furnace wall and the like is detected by use of two probes.

2. Description of the Prior Art

With reference to FIG. 11, description will be made on a prior art tube flaw detecting method for detecting a flawed portion in a heat exchanger tube and the like.

In a thermal power generation boiler, a furnace wall is constructed such that furnace wall tubes 2, which are heat exchanger tubes, are arranged in close proximity to each other. A furnace outer side is supported by a reinforcing plate 1 of metal material, a heat insulating material 3 is applied thereto for preventing heat loss from the furnace wall and a further outer side thereof is covered by a casing 8.

In a recent thermal power generation boiler, in order to effect load adjustments corresponding to differences in the power demands between day time and night time, there are made severe demands of frequent repeat starts and stops. Due to thermal stresses caused thereby, thermal fatigue cracks occur at welded portions of the reinforcing plate 1 and the furnace wall tube 2 on the outer surface of the furnace wall tube 2. Also, corrosion fatigue cracks occur in the vicinity of the welded portions on the inner surface of the furnace wall tube 2. Hence it is necessary to detect these cracks with certainty at periodic inspections and to renew the furnace wall tube 2.

In detecting these cracks occurring in the furnace wall tube 2, because the furnace outer side is covered by the heat insulating material 3 and the casing 8, it is impossible to apply an ultrasonic probe directly to the furnace wall tube 2 in that state.

In the prior art, therefore, crack inspection is done such that, though not illustrated, the heat insulating material 3 and casing 8 are once removed for access to a cracked portion. Alternatively, as shown in FIG. 11, water 11 is filled in the furnace wall tube 2. An ultrasonic transmitter probe 6 is applied to a surface on the furnace inner side of the furnace wall tube 2 to transmit an ultrasonic wave to pass through the tube wall of the furnace wall tube 2 and the water 11 in the furnace wall tube 2. A reflected wave, which is reflected by a circumferential crack 9, is detected by the same transmitter probe 6, which also has a receiver function at the same time.

Out of the above-mentioned two typical ways in the prior art for detecting a flaw portion in a heat exchanger tube and the like, the first mentioned way requires work for removing the heat insulating material and the casing portion and restoring them after the predetermined inspection has been done, which results in a problem of a high cost for carrying out the inspection. Also, the second mentioned way requires work for filling water in the furnace wall tube for inspection, which results in a problem that other work, such as welding work etc., cannot be done due to the existence of water while the inspection is being carried out.

SUMMARY OF THE INVENTION

It is therefore an object of the present invention to resolve such problems in the prior art, enabling one to carry out the inspection work more appropriately and with a high efficiency.

In order to attain the object, it is a feature of the present invention to provide a tube flaw detecting method using two probes. A transmitter probe and a receiver probe are juxtaposed in a circumferential direction on a tube surface on a furnace inner side. A transverse wave is caused to enter a tube wall at an angle of 10° to 50° inclined relative to a tube axis and an angle of refraction of 40° to 75°. An ultrasonic wave is thus propagated, repeating reflections at a tube inner surface and a tube outer surface, in a spiral direction on a tube circumferential surface to reach a crack which extends in the circumferential direction on a furnace outer side. A reflected wave from the crack thus propagates on an opposite side of the transmitter problem to be detected by the receiver probe.

That is, according to the present invention, by use of the pair of the transmitter probe and the receiver probe juxtaposed in the circumferential direction, the ultrasonic wave is transmitted from the transmitter probe to propagate, repeating reflections at the tube inner surface and tube outer surface, and is reflected at the crack extending in the circumferential direction to return, propagating likewise, to be received by the receiver probe, so that existence of the crack is confirmed. Thus, propagation becomes possible without the need to fill water as an ultrasonic transmission medium in the tube, and inspection work for a crack extending in the circumferential direction can be done with certainty with a simple construction.

It is also a feature of the present invention to provide a tube flaw detecting method using two probes where a transmitter probe and a receiver probe are spaced apart in an upward and downward direction on a tube surface on a furnace inner side. A transverse wave is caused to enter a tube wall with an angle of 40° to 80° inclined relative to a tube axis and an angle of refraction of 40° to 75°. An ultrasonic wave is caused to propagate, repeating reflections at a tube inner surface and a tube outer surface, in a spiral direction on a tube circumferential surface to reach a crack which extends in an axial direction on a furnace outer side, thus causing a reflected wave from the crack to propagate on the same side of the transmitter probe to be detected by the receiver probe.

That is, according to the present invention, by use of the pair of the transmitter probe and the receiver probe spaced apart in the upward and downward direction, an ultrasonic wave is transmitted from the transmitter probe to propagate, repeating reflections at the tube inner surface and tube outer surface, and is reflected at the crack extending in the axial direction to return, propagating likewise, to be received by the receiver probe, so that the existence of the crack is confirmed. Thus, propagation becomes possible without the need to fill water as an ultrasonic transmission medium in the tube, and inspection work for the crack extending in the axial direction can be done with certainty with a simple construction.

DESCRIPTION OF THE PREFERRED EMBODIMENTS

Figure 1:
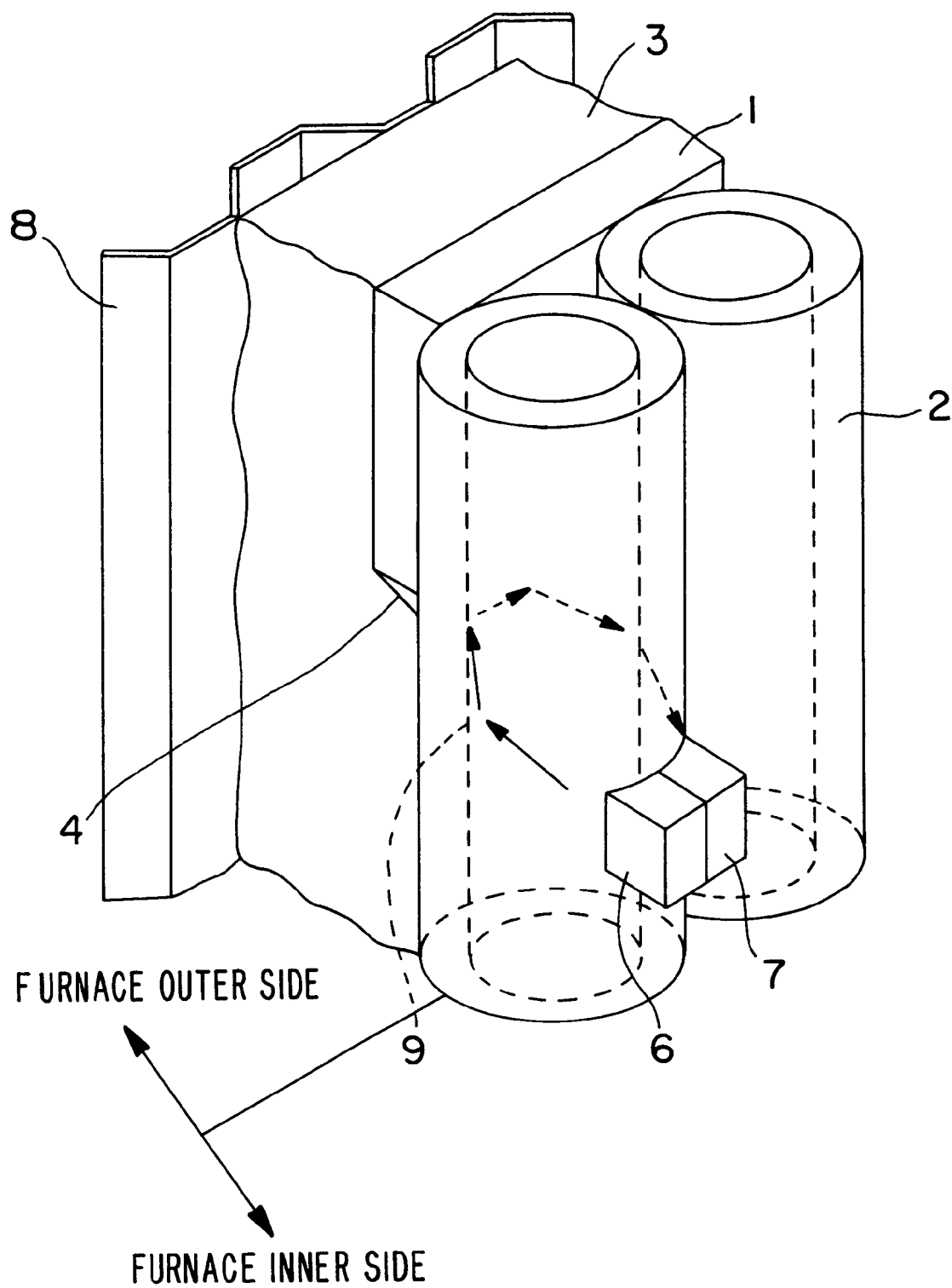
FIG. 1 is a perspective view explaining a detecting method of a crack which extends in a circumferential direction of a tube with respect to a first embodiment according to the present invention.
Figure 2:
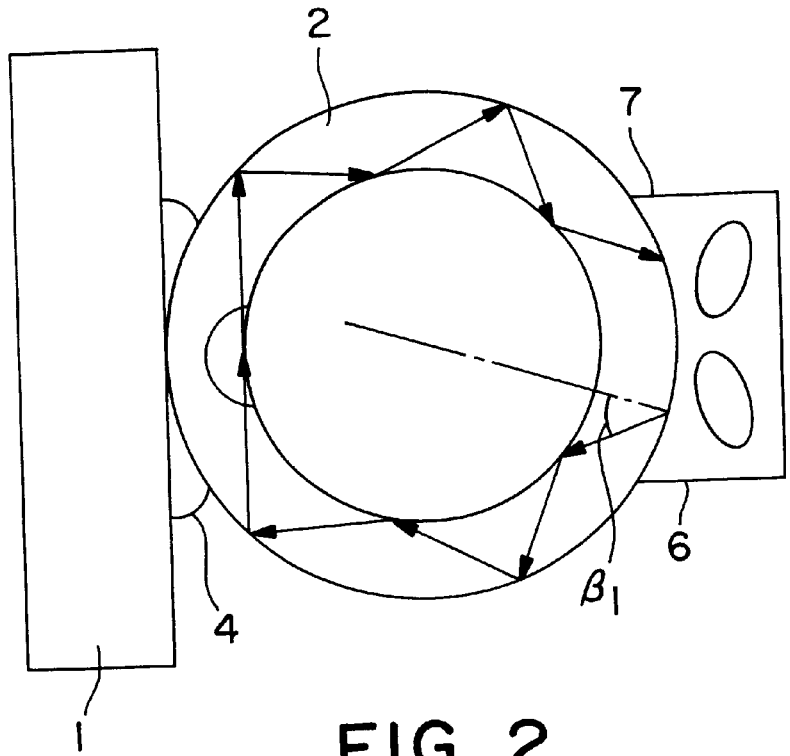
FIG. 2 is an explanatory plan view showing a state of ultrasonic propagation in a horizontal section of the tube of FIG. 1.
Figure 3:
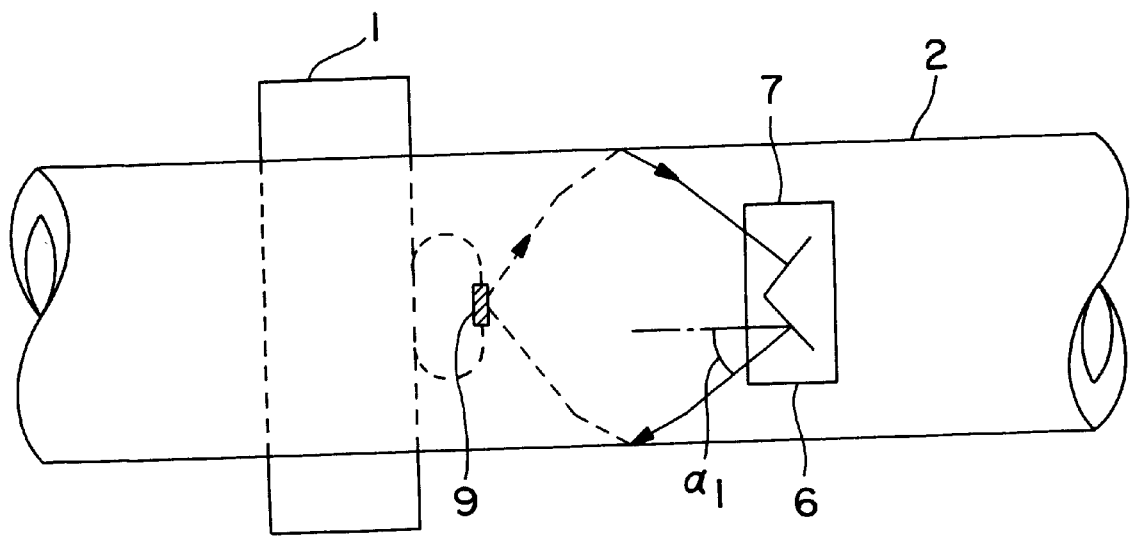
FIG. 3 is an explanatory side view showing a state of ultrasonic propagation in a side section of the tube of FIG. 1.
Figure 4:
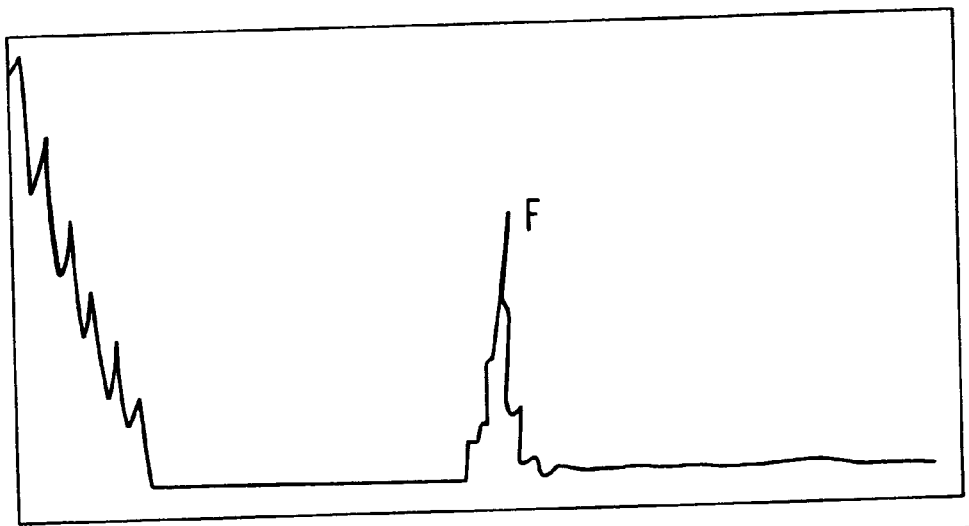
FIG. 4 is a flaw detection graph showing a case where there is a crack as a result of detection by the first embodiment of FIG. 1.
Figure 5:
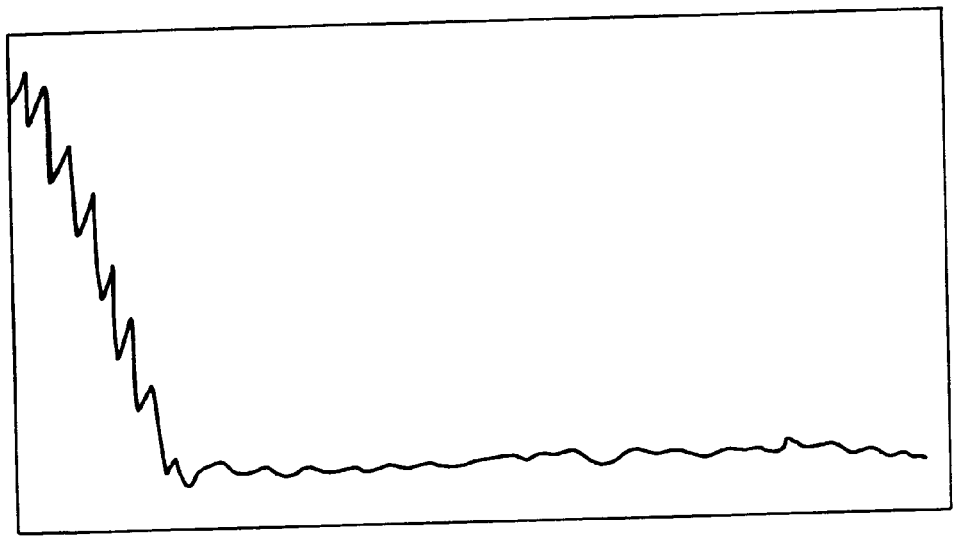
FIG. 5 is a flaw detection graph showing a case of no crack as a result of detection by the first embodiment of FIG. 1.
Figure 6:
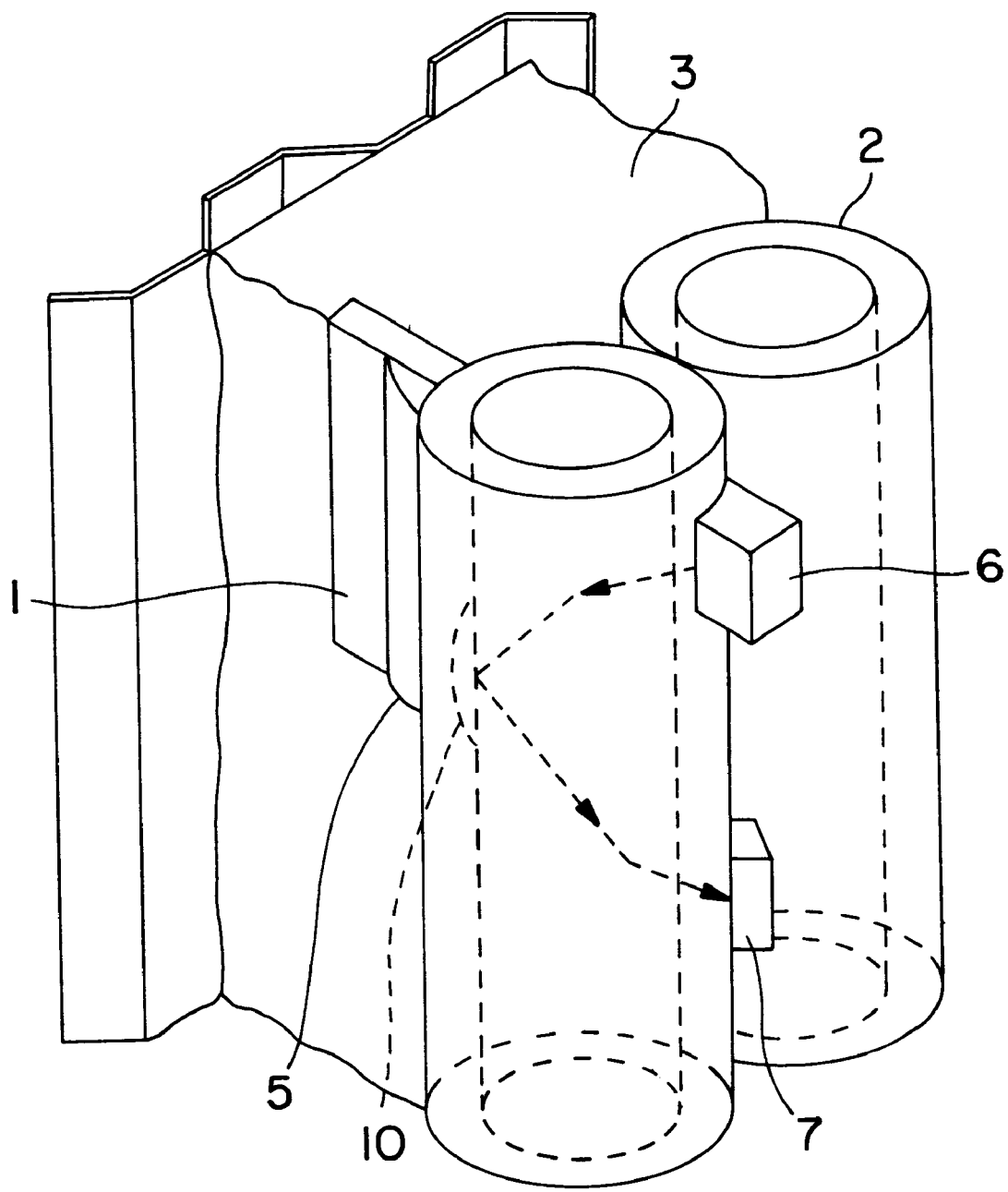
FIG. 6 is a perspective view explaining a detecting method of a crack which extends in an axial direction of a tube with respect to a second embodiment according to the present invention.

A first embodiment according to the present invention will be described with reference to FIGS. 1 to 5. FIG. 1 is a perspective view explaining a crack detecting method with respect to the first embodiment. FIG. 2 is an explanatory plan view in section of one furnace wall tube taken from the first embodiment and FIG. 3 is an explanatory side view taken in section of the furnace wall tube of FIG. 2, wherein FIGS. 2 and 3 explain a state of ultrasonic propagation with repeated reflections. FIGS. 4 and 5 are flaw detection graphs in a case of yes or no crack as a result of flaw detection.

It is to be noted that the same portions as shown in the prior art are given same numerals in the figures, and features in the present embodiment will be described with repeated descriptions being omitted to the extent possible.

In the present embodiment, a boiler furnace wall tube 2 of an outer diameter of 38.1 mm and a tube thickness of 5.5 mm is used, and a circumferential crack 9 which extends in the circumferential direction along a circumferential welded portion 4 (an expected crack occurring position) of the furnace wall tube 2 is going to be detected.

A transmitter probe 6 and a receiver probe 7, abutting back to back on each other, are disposed on the furnace wall tube 2, being juxtaposed in the circumferential direction.

S The transmitter probe 6 and the receiver probe 7 are both ultrasonic probes. An ultrasonic transverse wave is transmitted from the transmitter probe 6, which is an ultrasonic angle probe for transmission, disposed lower than a crack occurring position of the circumferential crack 9 to be detected on a surface on a furnace inner side of the furnace wall tube 2. The ultrasonic transverse wave enters the surface with an angle $\alpha_1$ of 40° relative to a tube axis and an angle of refraction $\beta_1$ of 60°.

The ultrasonic wave propagates, repeating reflections in a tube wall of the furnace wall tube 2 as shown by arrows in FIGS. 2 and 3, from the furnace inner side to a furnace outer side and from a lower part to an upper part in a spiral direction on a circumferential surface of the furnace wall tube 2.

If there is a circumferential crack 9 at the circumferential directional welded portion 4 on the furnace outer side, the ultrasonic wave is reflected there to propagate, repeating reflections, from the upper part to the lower part reversely to the direction along which it has entered and propagated and is received by the receiver probe 7. Thus, as shown in FIG. 4, a peak F is marked and a wave shape of flaw detection which shows a state of yes (there is a crack) is observed.

If there is no circumferential crack 9 at the circumferential directional welded portion 4 and the furnace outer side, the ultrasonic wave propagates as it is or it runs against a welded bead portion to be reflected there and to return to the transmitter probe 6, not reaching the receiver probe 7. Thus, as shown in FIG. 5, there is no peak marked, and a flaw detection wave shape shows a state of no crack.

According to the experiments made by the inventors here, a crack of a depth of up to 0.5 mm can be detected by this method. It has been confirmed that the method is effective enough from a practical point of view.

It is to be noted that although a case where the ultrasonic wave propagates from low to high with the angle of $\alpha_1$ was described above, it is also possible, naturally, to cause the ultrasonic wave to enter reversely in the direction from high to low.

Also, a case where the ultrasonic wave is caused to enter with an angle $\alpha_1$ of 40° relative to the tube axis and an angle of refraction $\beta_1$ of 60° was described, but these angles are appropriate for the furnace wall tube 2 of an outer diameter of 38.1 mm and a tube thickness of 5.5 mm, and other angles $\alpha_1$ and $\beta_1$ are to be selected corresponding to a different outer diameter and tube thickness. It is possible to determine $\alpha_1$ and $\beta_1$ selecting $\alpha_1$ in a range of 10° to 50° and $\beta_1$ in a range of 40° to 70°.

According to the present embodiment as described above, the circumferential crack 9 which occurs on the furnace outer side of the furnace wall tube 2 can be detected with certainty by the ultrasonic wave caused to propagate from the furnace inner side. A step for removing the heat insulating material 3 and the casing 8 and subsequently restoring them, as has been done in the prior art method, thereby becomes unnecessary, and the cost of work and time required for the inspection can be greatly reduced.

Figure 11:
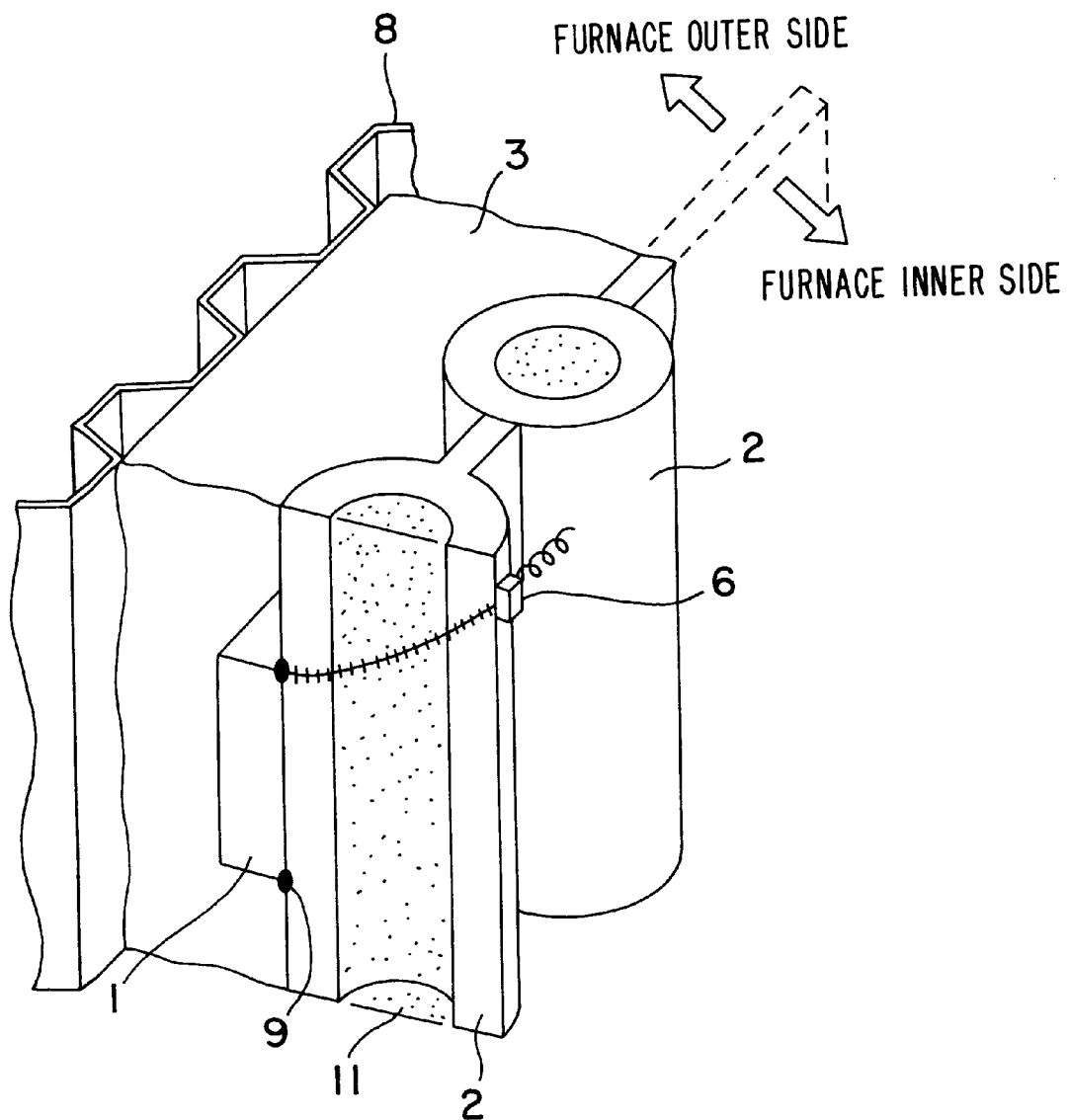
FIG. 11 is a perspective view for explaining one method in the prior art for detecting a crack in a tube.

Also, there is no need to fill water 11 in the furnace wall tube 2 as in the prior art method shown in FIG. 11. Thereby the work and time required therefor can be omitted, and the shortcoming that welding work cannot be done simultaneously with the inspection work due to the existence of the water 11 can be eliminated.

Next, a second embodiment according to the present invention will be described with the reference to FIGS. 6 to 10. FIGS. 6, 7, 8, 9 and 10 correspond to FIGS. 1, 2, 3, 4 and 5, respectively, showing the first embodiment. A substantial portion of the construction of the second embodiment is the same as or common to the first embodiment and similar to the described prior art. The same or common portions are given the same numerals in the figures and features in the present embodiment will be described with repeated description omitted to the extent possible.

In the present embodiment also, like the first embodiment, a boiler furnace wall tube 2 of an outer diameter of 38.1 mm and a tube thickness of 5.5 mm is used. An axial crack 10 occurs at a tube axial directional welded portion 5 of the furnace wall tube 2 as a portion to be inspected and is going to be detected.

A transmitter probe 6 and a receiver probe 7 are disposed up and down in the tube axial direction with a space between them on a surface on a furnace inner side of the furnace wall tube 2. The transmitter probe 6 is an ultrasonic angle probe for transmission and is disposed above a crack occurring position. An ultrasonic transverse wave is transmitted so that it enters the surface with an angle $\alpha_2$ of 70° relative to the tube axis and an angle of refraction $\beta_2$ of 50°.

Figure 7:
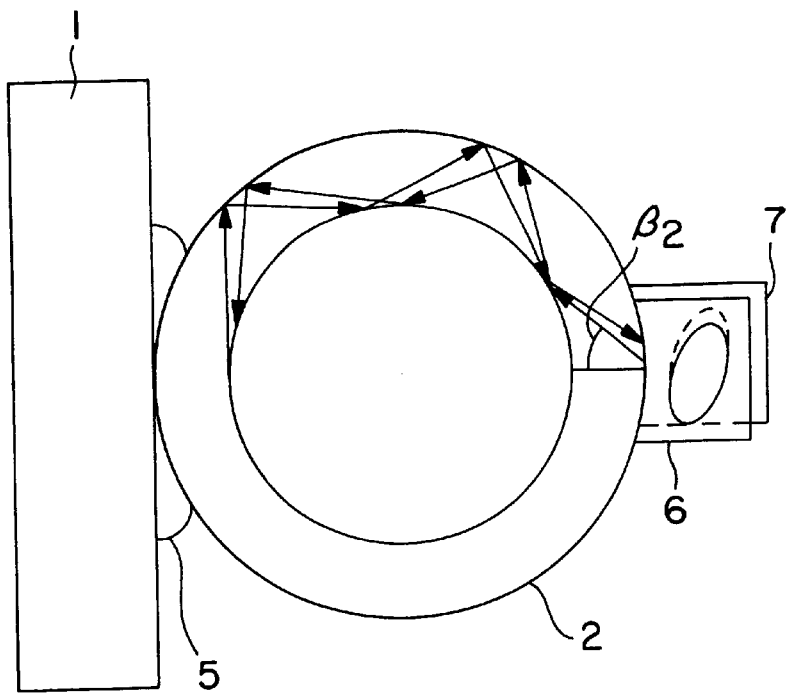
FIG. 7 is an explanatory plan view showing a state of ultrasonic propagation in a horizontal section of the tube of FIG. 1 for the second embodiment.
Figure 8:
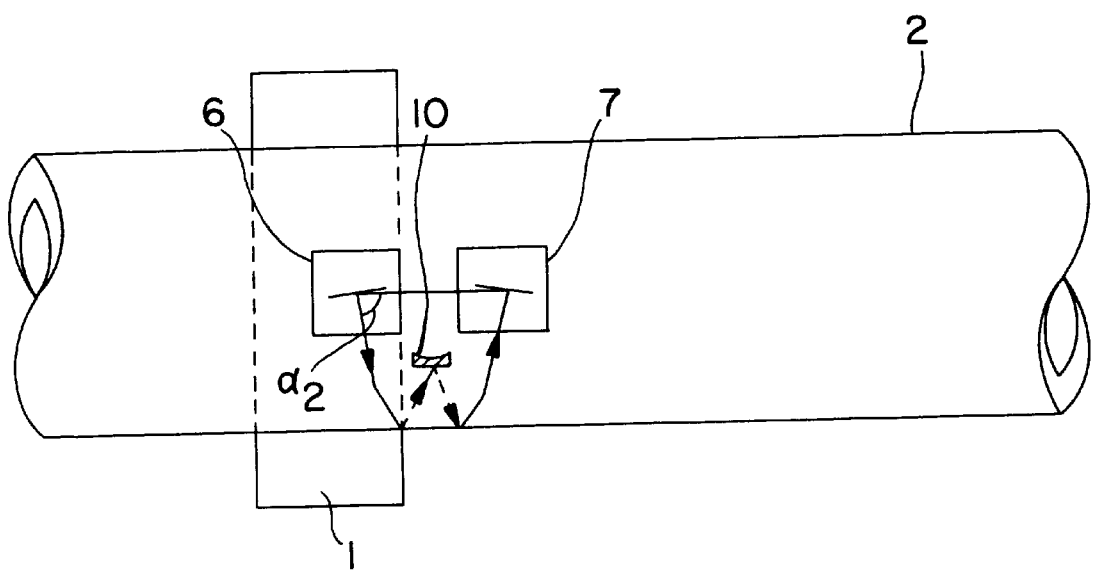
FIG. 8 is an explanatory side view showing a state of ultrasonic propagation in a side section of the tube of FIG. 1 for the second embodiment.

The ultrasonic wave propagates, repeating reflections in a tube wall of the furnace wall tube 2 as shown by arrows in FIGS. 7 and 8, from the furnace inner side to a furnace outer side and from an upper part to a lower part.

Figure 9:
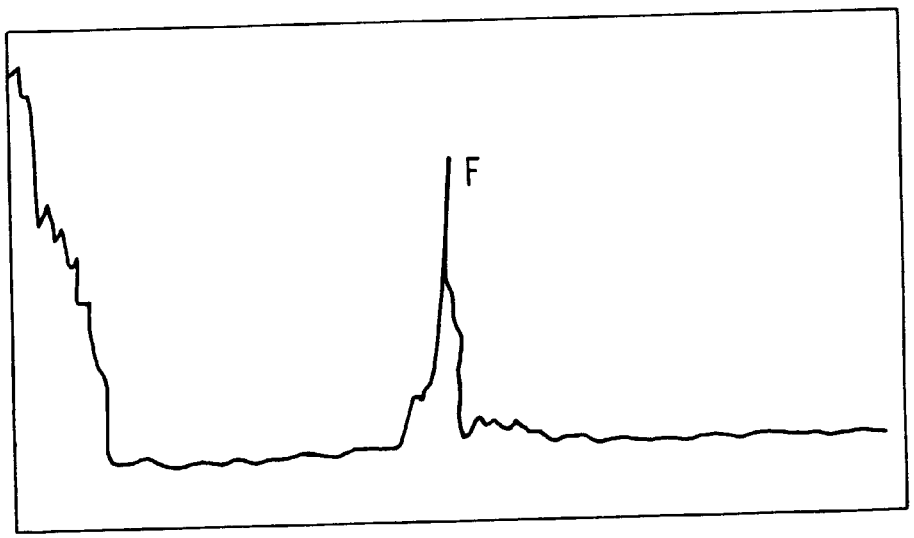
FIG. 9 is a flaw detection graph showing a case of where there is a crack as a result of detection by the second embodiment of FIG. 6.

If there is an axial crack 10 at the tube axial directional welded portion 5 on the furnace outer side, the ultrasonic wave is reflected there to propagate, repeating reflections in a reverse direction to the direction along which it has entered and propagated and is received by the receiver probe 7, which is disposed lower than the crack occurring position to oppose the transmitter probe in an upward and downward direction. The crack occurring position is between the two probes. Thus, as shown in FIG. 9, a peak F is marked and a wave shape of flaw detection which shows a state of yes (there is a crack) is observed.

Figure 10:
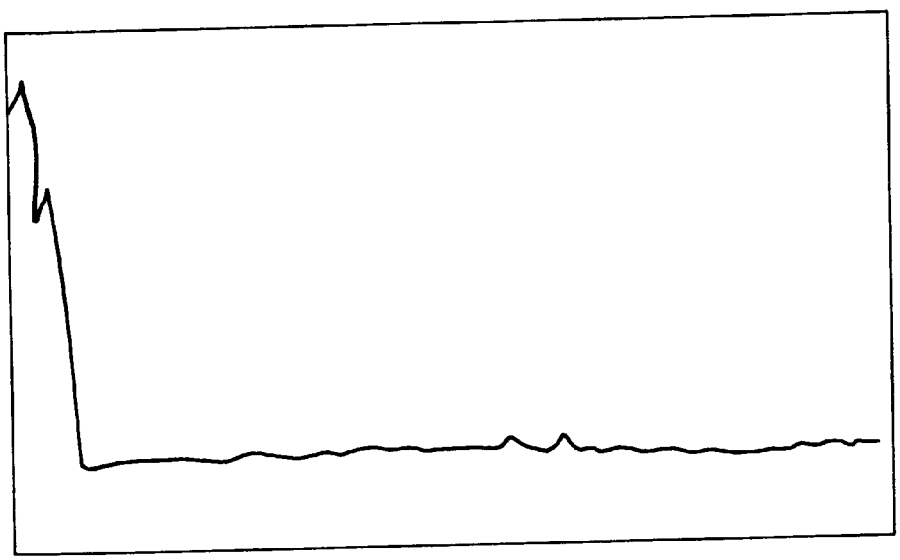
FIG. 10 is a flaw detection graph showing a case of no crack as a result of detection by the second embodiment of FIG. 6.

If there is no axial crack 10 at the tube axial directional welded portion 5 on the furnace outer side, the ultrasonic wave propagates as it is or it runs against welded bead portion to be reflected there and to return to the transmitter probe 6, not reaching the receiver probe 7. Thus, as shown in FIG. 10, there is no peak marked and a wave shape of flaw detection which shows a state of no crack is observed.

According to the experiments made by the inventors here, a crack of depth of up to 0.5 mm can be detected by this method. It has been conformed that the method is effective enough from a practical point of view.

It is to be noted that although a case where the ultrasonic wave propagates from high to low with the crack occurring position being in between was described above, it is also naturally possible to cause the ultrasonic wave to enter reversely in the direction from low to high.

Also, a case where the ultrasonic wave is caused to enter with an angle $\alpha_2$ of 70° relative to the tube axis and an angle of refraction $\beta_2$ of 50° was described, but these angles are appropriate for the furnace wall tube 2 of outer diameter of 38.1 mm and tube thickness of 5.5 mm. Other angles $\alpha_2$ and $\beta_2$ are to be selected corresponding to a different outer diameter and tube thickness. It is possible to determine $\alpha_2$ and $\beta_2$ selecting $\alpha_2$ in a range of 40° to 80° and $\beta_2$ in a range of 40° to 75°.

According to the present embodiment as described above, like the first embodiment, the axial crack 10 which occurs on the furnace outer side of the furnace wall tube 2 can be detected with certainty by the ultrasonic wave caused to propagate from the furnace inner side. A step for removing the heat insulating material 3 and the casing 8 and subsequently restoring them, as has been done in the prior art method, becomes unnecessary, and the cost for the work and time required for the inspection can be greatly reduced.

In the above, embodiments according to the present invention have been described with reference to the figures, but the present invention is not limited to these embodiments and, needless to mention, may have various modifications in the concrete construction within the scope of claims as set forth below.

According to the present invention, the tube flaw detecting method using two probes is constructed such that the transmitter probe and the receiver probe are juxtaposed in the circumferential direction on the tube surface on the furnace inner side, a transverse wave is caused to enter the tube wall with an angle of 10° to 50° inclined relative to the tube axis and an angle refraction of 40° to 75°, an ultrasonic wave is caused to propagate, repeating reflections at the tube inner surface and tube outer surface, in the spiral direction on the tube circumferential surface to reach a crack which extends in the circumferential direction. The reflected wave from the crack is caused to propagate on the opposite side of the transmitter probe and to be detected by the receiver probe.

That is, according to the present invention, by use of the pair of the transmitter probe and the receiver probe juxtaposed in the circumferential direction, the ultrasonic wave is transmitted from the transmitter probe to propagate, repeating reflections in the tube inner surface and tube outer surface, and is reflected at the crack extending in the circumferential direction to return, propagating likewise, to be received by the receiver probe, so that existence of the crack is confirmed. Thus, propagation becomes possible without the need to fill water as an ultrasonic transmission medium in the tube, and inspection work for a crack extending in the circumferential direction can be done with certainty with a simple construction.

Also, the step for removing the heat insulting material and the casing of the outer side and restoring them subsequently, as has been done in one prior art method, becomes unnecessary and there is no need to fill water as an ultrasonic transmission medium in the furnace wall tube, as has been done in another prior art method. Thereby the cost for the work and time required therefor can be greatly reduced. The shortcoming that welding work cannot be done simultaneously with the inspection work due to the existence of water can also be avoided; and a simple and most suitable inspection method can be obtained.

According to another aspect of the present invention, the tube flaw detecting method using two probes is constructed such that the transmitter probe and the receiver probe are spaced there between in the upward and downward directions on the tube surface on the furnace inner side, a transverse wave is caused to enter the tube wall with an angle of 40° to 80° inclined relative to the tube axis and an angle of refraction of 40° to 75°, an ultrasonic wave is caused to propagate, repeating reflections at the tube inner surface and tube outer surface, in the spiral direction on the tube circumferential surface to reach a crack with extends in the axial direction, and the reflected wave from the crack is caused to propagate on the same side of the transmitter probe to be detected by the receiver probe.

That is, according to the present invention, by use of the pair of the transmitter probe and the receiver probe spaced apart in the upward and downward direction, an ultrasonic wave is transmitted from the transmitter probe to propagate, repeating reflections at the tube inner surface and tube outer surface, and is reflected at the crack extending in the axial direction to return, propagating likewise, to be received by the receiver probe, so that the existence of the crack is confirmed. Thus, propagation becomes possible without the need to fill water as an ultrasonic transmission medium in the tube and inspection work for the crack extending in the axial direction can be done with certainty with a simple construction.

While in the first mentioned embodiment of the present invention the existence of a crack which extends in the circumferential direction in confirmed, the second mentioned embodiment of the present invention inspects a crack which extends in the axial direction with certainty, and an excellent and practical inspection method can be obtained, like the first mentioned embodiment.

What is claimed is:

1. A tube flaw detecting method for detecting a circumferentially extending crack in a furnace tube, the furnace tube having a tube wall, a tube inner surface, a tube outer surface, a furnace inner side, a furnace outer side and a tube axis, and said method comprising:

disposing a transmitter probe and a receiver probe so that said transmitter probe and said receiver probe are juxtaposed in a circumferential direction of the tube on the furnace inner side of the tube;

propagating an ultrasonic transverse wave with the transmitter probe so that the ultrasonic transverse wave enters the tube wall with an angle of 10° to 50° relative to the tube axis and an angle of refraction of 40° to 75° and propagates in a spiral direction of the furnace tube in the tube wall such that the ultrasonic transverse wave travels both circumferentially of the furnace tube through the tube wall and axially through the tube wall of the furnace tube, repeatedly reflecting at the tube inner surface and the tube outer surface, so as to be able to reach a crack that might extend in the circumferential direction on the furnace outer side of the furnace tube; and detecting ultrasonic waves with the receiver probe so that an ultrasonic wave reflected from the crack to propagate on an opposite side of the tube from the transmitter probe is detected by the receiver probe.

2. The method of claim 1, wherein said propagating comprises having the ultrasonic wave enter the tube wall at an angle of 40° relative to the tube axis and at an angle of refraction of 60°.

3. The method of claim 2, wherein the furnace tube has an outer diameter of 38.1 mm and a tube thickness of 5.5 mm.

4. The method of claim 1, wherein the furnace tube has an outer diameter of 38.1 mm and a tube thickness of 5.5 mm.

5. The method of claim 1, wherein:

said disposing further comprises disposing said transmitter probe and said receiver probe on the tube so that the probes are axially spaced along the tube from an expected crack occurring position; and said propagating further comprises propagating the ultrasonic wave in an axial direction toward the crack occurring position.

6. A tube flaw detecting method for detecting a circumferentially extending crack in a furnace tube mounted on a furnace wall, the furnace tube having a tube wall, a tube inner surface, a tube outer surface, a furnace inner side directed toward the inside of a furnace, a furnace outer side directed toward the outside of the furnace and the furnace wall, and a tube axis, and said method comprising:

disposing a transmitter probe and a receiver probe so that said transmitter probe and said receiver probe are juxtaposed in a circumferential direction of the furnace tube on the furnace inner side of the furnace tube;

propagating an ultrasonic transverse wave with the transmitter probe so that the ultrasonic transverse wave enters the tube wall with an angle of 10° to 50° relative to the tube axis and an angle of refraction of 40° to 75° and propagates in a spiral direction of the furnace tube in the tube wall such that the ultrasonic transverse wave travels both circumferentially of the furnace tube through the tube wall and axially through the tube wall of the furnace tube, repeatedly reflecting at the tube inner surface and the tube outer surface, so as to be able to reach a crack that might extend in the circumferential direction on the furnace outer side of the furnace tube; and detecting ultrasonic waves with the receiver probe so that an ultrasonic wave reflected from the crack on the furnace outer side of the furnace tube that extends in the circumferential direction of the furnace tube to propagate on an opposite side of the furnace tube from the transmitter probe is detected by the receiver probe.

7. The method of claim 6, wherein said propagating comprises having the ultrasonic wave enter the tube wall at an angle of 40° relative to the tube axis and at an angle of refraction of 60°.

8. The method of claim 7, wherein the furnace tube has an outer diameter of 38.1 mm and a tube thickness of 5.5 mm.

9. The method of claim 6, wherein the furnace tube has an outer diameter of 38.1 mm and a tube thickness of 5.5 mm.

10. The method of claim 6, wherein:

said disposing further comprises disposing said transmitter probe and said receiver probe on the furnace tube so that the probes are axially spaced along the furnace tube from an expected crack occurring position; and said propagating further comprises propagating the ultrasonic wave in an axial direction toward the crack occurring position.

11. A tube flaw detecting method for detecting an axially extending crack in a furnace tube, the furnace tube having a tube wall, a tube inner surface, a tube outer surface, a furnace inner side, a furnace outer side and a tube axis, and said method comprising:

disposing a transmitter probe and a receiver probe so that said transmitter probe and said receiver probe are axially spaced apart from each other on the furnace inner side of the furnace tube;

propagating an ultrasonic transverse wave with the transmitter probe so that the ultrasonic transverse wave enters the tube wall with an angle of 40° to 80° relative to the tube axis and an angle of refraction of 40° to 75° and propagates in a spiral direction of the furnace tube in the tube wall such that the ultrasonic transverse wave travels both circumferentially of the furnace tube through the tube wall and axially through the tube wall of the furnace tube, repeatedly reflecting at the tube inner surface and the tube outer surface, so as to be able to reach a crack that might extend in an axial direction on the furnace outer side of the tube; and detecting ultrasonic waves with the receiver probe so that an ultrasonic wave reflected from the crack to propagate on the same side of the tube as the transmitter probe is detected by the receiver probe.

12. The method of claim 11, wherein said propagating comprises having the ultrasonic wave enter the tube wall at an angle of 40° relative to the tube axis and at an angle of refraction of 60°.

13. The method of claim 12, wherein the furnace tube has an outer diameter of 38.1 mm and a tube thickness of 5.5 mm.

14. The method of claim 11, wherein the furnace tube has an outer diameter of 38.1 mm and a tube thickness of 5.5 mm.

15. The method of claim 11, wherein:

said disposing further comprises disposing said transmitter probe and said receiver probe on the tube so that the probes are axially spaced along the tube on opposite sides of an expected crack occurring position; and said propagating further comprises propagating the ultrasonic wave in an axial direction toward the crack occurring position.

16. A tube flaw detecting method for detecting an axially extending crack in a furnace tube mounted on a furnace wall, the furnace tube having a tube wall, a tube inner surface, a tube outer surface, a furnace inner side directed toward the inside of a furnace, a furnace outer side directed toward the outside of the furnace and the furnace wall, and a tube axis, and said method comprising:

disposing a transmitter probe and a receiver probe so that said transmitter probe and said receiver probe are axially spaced apart from each other on the furnace inner side of the furnace tube;

propagating an ultrasonic transverse wave with the transmitter probe so that the ultrasonic transverse wave enters the tube wall with an angle of 40° to 80° relative to the tube axis and an angle of refraction of 40° to 75° and propagates in a spiral direction of the furnace tube in the tube wall such that the ultrasonic transverse wave travels both circumferentially of the furnace tube through the tube wall and axially through the tube wall of the furnace tube, repeatedly reflecting at the furnace tube inner surface and the furnace tube outer surface, so as to be able to reach a crack that might extend in an axial direction on the furnace outer side of the furnace tube; and detecting ultrasonic waves with the receiver probe so that an ultrasonic wave reflected from the crack on the furnace outer side of the furnace tube that extends in the axial direction of the tube to propagate on an opposite side of the furnace tube from the transmitter probe is detected by the receiver probe.

17. The method of claim 16, wherein said propagating comprises having the ultrasonic wave enter the tube wall at an angle of 40° relative to the tube axis and at an angle of refraction of 60°.

18. The method of claim 17, wherein the furnace tube has an outer diameter of 38.1 mm and a tube thickness of 5.5 mm.

19. The method of claim 16, wherein the furnace tube has an outer diameter of 38.1 mm and a tube thickness of 5.5 mm.

20. The method of claim 16, wherein:

said disposing further comprises disposing said transmitter probe and said receiver probe on the furnace tube so that the probes are axially spaced along the furnace tube on opposite sides of an expected crack occurring position; and said propagating further comprises propagating the ultrasonic wave in an axial direction toward the crack occurring position.

* * * * *